United States Patent [19]

Marissal

[11] 4,187,291

[45] Feb. 5, 1980

[54] COSMETIC COMPOSITION FOR THE SKIN

[75] Inventor: Janine Marissal, Monte Carlo, Monaco

[73] Assignee: Biotherm, Monte Carlo, Monaco

[21] Appl. No.: 794,646

[22] Filed: May 6, 1977

[30] Foreign Application Priority Data

May 7, 1976 [LU] Luxembourg .......................... 74900

[51] Int. Cl.² ...................... A61K 37/48; A61K 35/78
[52] U.S. Cl. ...................................... 424/94; 424/195
[58] Field of Search .................................. 424/195, 94

[56] References Cited

U.S. PATENT DOCUMENTS

| | | | |
|---|---|---|---|
| 3,170,916 | 2/1965 | Dziengel | 424/195 |
| 3,766,166 | 10/1973 | Menssen et al. | 424/195 |

FOREIGN PATENT DOCUMENTS 609811 10/1948 United Kingdom ...................... 424/365

OTHER PUBLICATIONS

Chemical Abstracts, vol. 54, 9097h, vol. 80, 19402f, vol. 81, 126691s & 68555n, vol. 81, 29567y, vol. 82, 175274n, vol. 83, 10743x, & 103237a, vol. 83, 203535q & 209332t, vol. 84, 38714h & vol. 84, 21961p.

*Primary Examiner*—Donald B. Moyer
*Attorney, Agent, or Firm*—Cushman, Darby & Cushman

[57] ABSTRACT

A cosmetic composition for the skin comprises in an appropriate cosmetic vehicle or base at least one non-hormonal iodinated organic compound, at least one diffusion enzyme and at least one anti-inflammatory or anti-edematous acting agent.

11 Claims, No Drawings

COSMETIC COMPOSITION FOR THE SKIN

The present invention relates to a cosmetic composition for the skin and, in particular, to a composition possessing both a slenderizing and anti-cellulitic action.

Numerous compositions have previously been proposed for the prevention of cellulitis and the accumulation of folds of fat found on some people, especially on their hips and thighs.

Thus far, however, these known compositions have not provided full satisfaction.

It has now been found that it is possible to fight cellulitis and at the same time obtain a slenderizing action by using a cosmetic composition which incorporates three active components heretofore used separately, thereby obtaining a potentiating action.

Tests conducted using the novel composition of this invention revealed their excellent slenderizing and anti-cellulitic action.

Thus, the present invention relates to a cosmetic composition for the skin comprising in an appropriate cosmetic base:

(i) at least one non-hormonal iodinated organic compound;
(ii) at least one diffusion enzyme; and
(iii) at least one anti-inflammatory and/or anti-edematous acting agent.

The non-hormonal iodinated organic compound can have a variety of structures. Preferably, in accordance with the present invention, this component is an iodinated protein such as iodinated peptone or iodinated casein.

As iodinated casein, those commercially available under the names "Iodo Casein", and "Protamone", containing 5 to 6 weight percent iodine, are especially suited for use in the present invention.

In accordance with the invention, it is also possible to use, as the iodinated organic compound, iodinated derivatives obtained from fatty acids or unsaturated fatty acid esters or mixtures thereof, such as ethyl diodobrassidate, better known as "Iodobrassid" or "Lipoiodine", or diodoricinstearolic acid, known as "Periodyl".

The iodinated organic compound can also be an iodinated vegetable oil such as, for example, the product known as "Lipiodol", containing 38 to 42% combined iodine or the alkyl esters of iodinated poppy-seed oil, and in particular, the ethyl ester known as "Ethiodol", containing approximately 37 to 40% combined iodine.

The iodinated organic compound can also be an aromatic compound, and particularly those compounds employed as contrasting agents for X-rays, and even more particularly those compounds having the following formula:

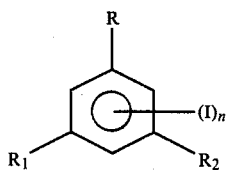

wherein:

n is 1, 2 or 3 in the ortho or para position relative to R;

R is —Z—COR$_3$ wherein Z is a simple bond or a branched or linear alkyl having 1 to 12 carbon atoms, optionally interrupted by a heteroatom such as N or O, and R$_3$ represents OH, OM wherein M is an alkaline or alkaline-earth metal or an amine, OR$_4$ wherein R$_4$ is alkyl containing 1 to 5 carbon atoms,

wherein r' and r", identical or different, represent hydrogen, alkyl containing 1 to 6 carbon atoms, phenyl or —(CH$_2$)$_m$—COOR$_5$ wherein m is 1–4 and R$_5$ is a hydrogen or alkyl containing 1 to 5 carbon atoms; and R$_1$ and R$_2$, either identical or different, represent hydrogen, NH$_2$, CONHCH$_3$ or —N=CH—N(CH$_3$)$_2$.

Specific examples of these compounds include:

2,4,6-triodo-3-(dimethylaminomethylene) amino hydrocinnamic acid, 2,4,6-triodo-3-amino α-ethyl hydrocinnamic acid (Iopanoic acid), 2,4,6-triodo-3-hydroxy α-ethyl hydrocinnamic acid (Iophenoxic acid), 2,4,6-triodo-5-acetamido-N-methyl isophthalamic acid (Iothalamic acid), 2-(2,4,6-triodo phenoxy) butyric acid (Phenobutiodil), the sodium salt of 2,4,6-triodo-3,5-diacetamido benzoic acid (sodium diatrizoate), the sodium salt of o-iodohippuric acid, ethyl 10-(p-iodophenyl) undecylate (Iophendylate), the methyl glucamine salt of 2,4,6-triodo-3-acetamido benzoic acid, and the methyl glucamine salt of 2,4,6-triodo-3,5-diacetamido benzoic acid.

The iodinated organic compound can also be a compound having the formula:

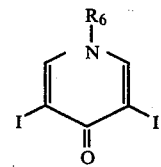

wherein R$_6$ represents hydrogen or hydroxy alkyl having 2 to 6 carbon atoms.

Included among these compounds are: 3-5-diiodo 4-pyridone (1H) (Iopydone) and 3-5-diiodo-1-(2,3-dihydroxypropyl)-4-pyridone (1H) (Iopydol).

Generally, the iodinated organic compound is present in the composition in an amount sufficient so that the composition contains between 1 to 15%, preferably from 1.5 to 6%, combined iodine by weight, based on the total weight of the composition.

In accordance with the present invention, the diffusion enzyme is a mucopolysaccharidase, and more specifically, thiomucase and hyaluronidase, and particularly hyaluronidase known commercially as "Hyalase".

This compound is a lyophilized extract of bull testicles, in the form of an amorphous, yellowish powder. Its rate of water solubility is 5 g/liter.

In the compositions according to the present invention, the diffusion enzyme is present in an amount sufficient so that the composition contains between 500 and 50,000 turbidity-reducing units (TRU).

Lastly, the anti-inflammatory and/or anti-edematous substance is, according to the present invention, preferably a saponin having a steroid skeleton, and more specifically, escine (α-escine) in the form of a free acid or in the form of an horsechestnut extract containing about 70% escine. Obviously other saponins of this type can be used in the compositions of the present invention. The amount of steroid-skeleton saponin generally ranges between 0.2 and 2 percent and preferably between 0.5 to 1.5 percent by weight of the composition.

The compositions of the present invention can be provided in various forms, such as particularly, emulsions, creams, milks, gels, aerosol foams and the like.

In addition to the three active components defined above, the compositions of this invention can also contain other, conventional adjuvants for this type of composition such as, perfumes, coloring agents, preservative agents and the like.

The present invention also relates to a skin-treatment process for combatting or alleviating cellulitis and reducing folds of fat comprising rubbing the composition of the present invention on those parts of the body to be treated in an amount sufficient to alleviate or combat cellulitis or to reduce the folds of fat.

Generally, the length of treatment is variable, but highly satisfying results can be achieved when the treatment is carried out on a daily basis for about 1 to 4 months.

The following non-limiting examples are given to illustrate the present invention. Unless otherwise stated, all parts and percentages are by weight.

EXAMPLE I

A slenderizing cream is prepared according to the invention by mixing the following components:

| | |
|---|---|
| Triple pressure stearic acid | 3 g |
| Isopropyl myristate | 5 g |
| Cetyl alcohol | 3 g |
| Glycerol monostearate | 3 g |
| Polyoxyethylenated sorbitan mono-oleate | 3 g |
| Petrolatum oil | 5 g |
| Monopropylene glycol | 4 g |
| Sorbitol | 3 g |
| Methyl parahydroxybenzoate | 0.3 g |
| Ethyl ester of poppy seed oil, 40% iodinated | 4 g |
| Mucopolysaccharidase (Hyalase) | 1200 TRU |
| α-escine, free acid | 1 g |
| Perfume | 0.5 g |
| Sterile demineralized water, sufficient for | 100 g |

Applied evenly on the hips and thighs daily for 4 to 6 weeks, this cream decreases the folds of fat.

A similar slenderizing cream is prepared by replacing the ethyl ester of poppy seed oil, 40% iodinated in the above formulation with an essentially equivalent amount of the iodinated vegetable oil known as "Lipiodol" containing 38-42% combined iodine.

EXAMPLE II

A composition in the form of an emulsion is prepared according to the invention by mixing the following components:

| | |
|---|---|
| Water-soluble purcelin oil | 1 g |
| Polyoxyethylenated ricin oil | 1 g |
| Monopropylene glycol | 10 g |
| Polyethylene glycol | 5 g |
| Ethyl alcohol, 95° titer | 2 g |

| -continued | |
|---|---|
| Propyl parahydroxybenzoate | 0.3 g |
| Ethyl ester of poppy seed oil 40% iodinated | 5 g |
| α-escine, free acid | 1 g |
| Mucopolysaccharidase (Hyalase) | 1500 TRU |
| Sterile demineralized water, q.s.p. | 100 g |

Daily application of this emulsion on the hips and thighs for 4 to 6 weeks results in a considerable decrease in cellulitis and the fatty rolls.

A similar composition is prepared by replacing the hyaluronidase known as "Hyalase" in the above formulation with a sufficient amount of thiomucase so that the composition contains 1500 TRU.

EXAMPLE III

A slenderizing gel is prepared according to the invention by mixing the following components:

| | |
|---|---|
| Carbopol 940 (carboxy polymethylene) | 0.4 g |
| Triethanolamine (85%) | 0.4 g |
| Monopropylene glycol | 8 g |
| Polyethylene glycol (MW = 400) | 5 g |
| Propyl parahydroxybenzoate | 0.3 g |
| Ethyl ester of poppy seed oil, 40% iodinated, viscosity at 20° C. = 1.5 to 2.5 poises | 4 g |
| α-escine, free acid | 1 g |
| Mucopolysaccharidase (Hyalase) | 1500 TRU |
| Sterile demineralized, water q.s.p. | 100 g |

This gel give excellent results when applied daily for about 4 to 6 weeks.

EXAMPLE IV

A slenderizing milk is prepared according to the invention by mixing the following components:

| | |
|---|---|
| Petrolatum oil | 10 g |
| Isopropyl palmitate | 2 g |
| Liquid lanolin | 1 g |
| Triple pressure stearic acid | 2.5 g |
| Glycerol monostearate | 2.5 g |
| Triethanolamine (85%) | 0.8 g |
| Monopropylene glycol | 2 g |
| Ethyl diodo-brassidate (Lipoiodine) | 6 g |
| Horse-chestnut extract containing 70% escine | 1 g |
| Methyl parahydroxybenzoate | 0.3 g |
| Hyaluronidase | 2000 TRU |
| Perfume | 0.3 g |
| Sterile demineralized water, q.s.p. | 100 g |

Daily application of this milk on the hips and thighs for about 5 weeks results in a considerable decrease in cellulitis and the fatty rolls.

A similar slenderizing milk is prepared by replacing the ethyl diodo-brassidate (Lipoiodine) in the above formulation with an essentially equivalent amount of diodo-ricinstearolic acid, known as "Periodyl".

Comparative tests were conducted to demonstrate the excellent activity of the composition of the present invention, and in particular the potentiating action derived from the combination of the three active components.

One hundred and eighty women with unsightly hips and thighs were divided into three groups of 60 women each. For each group the experiment lasted two months. Measurements were taken at the start of the test and two months after application of the composition of this invention. Each woman was instructed imperatively to apply the composition every day over the area of the hips and on the upper two-thirds of the thighs, to massage it in lightly and not to change her eating habits or daily routine in order not to introduce factors detrimental to the evaluation of the tests.

After the second month, the effectiveness of the composition tested was evaluated by means of measurements which were compared to the measurements taken at the beginning of the treatment.

The first group, group A, was given a placebo cream so as to determine whether the effect of the massage could in itself have an effect on slenderizing.

The composition of this placebo cream was as follows:

| Triple pressure stearic acid | 3 g |
|---|---|
| Isopropyl myristate | 5 g |
| Cetyl alcohol | 3 g |
| Glycerol monostearate | 3 g |
| Polyoxyethylenated sorbitan mono-oleate | 3 g |
| Petrolatum oil - Codex | 5 g |
| Monopropylene glycol | 4 g |
| Sorbitol | 3 g |
| Methyl parahydroxybenzoate | 0.3 g |
| Perfume | 0.5 g |
| Sterile demineralized water | 100 g |

The results obtained on the 60 women in group A, after two months, were as follows:

| GROUP A | Loss of 2.5 to 3 cm | Loss of 1 to 2 cm | No Loss | TOTAL |
|---|---|---|---|---|
| Hips | 2 women | 3 women | 55 women | 60 |
| Thighs | 1 woman | 39 women | 20 women | 60 |

The 60 women in group B were given a cream which was identical to the placebo cream used by the women in group A, but to which were added 4 g of ethyl ester of poppy seed oil, 40% iodinated, and sufficient Hyalase, so that the composition had 1200 TRU.

The results obtained on these 60 women in group B were as follows:

| GROUP B | Loss of 4 cm | Loss of 2.5 to 3 cm | Loss of 1 to 2 cm | No loss | TOTAL |
|---|---|---|---|---|---|
| Hips | 4 women | 10 women | 30 women | 16 women | 60 |
| Thighs | — | 1 woman | 39 women | 20 women | 60 |

The 60 women in group C used a composition according to the present invention, i.e., a composition such as the one used by the women in group B but to which 1 g of α-escine in the form of its free acid was added.

After two months of treatment, the results obtained on these 60 women were as follows:

| GROUP C | Loss of 4 to 5 cm | Loss of 2.5 to 3.5 cm | Loss of 1 to 2 cm | No loss | TOTAL |
|---|---|---|---|---|---|
| Hips | 10 women | 19 women | 22 women | 9 women | 60 |
| Thighs | — | 4 women | 45 women | 11 women | 60 |

As can be seen from the above results, the placebo cream had essentially no slenderizing effect on the hips, although it did provide an extremely slight slenderizing action on the thighs.

On the other hand, the composition employed by the women in group B containing the ethyl ester of 40% iodinated poppy seed oil and Hyalase provided perceptible slenderizing effect, particularly on the hips, compared to the placebo composition.

However, concerning the effect on the thighs, the results are identical to those observed on the women in group A.

On the other hand, excellent results were observed on the women treated with the composition according to the present invention. In fact, 51 of the 60 women lost from 1 to 5 cm around the hips, 29 of them losing more than 2.5 cm. Similarly, a loss on the thighs was observed which ranged between 1 to 3.5 cm for 49 of these 60 women.

These test, particularly the comparison of compositions used by the women in groups B and C, clearly show that there is a potentiating action among the active ingredients.

What is claimed is:

1. A composition for treating cellulitis or folds of fat comprising in a cosmetically acceptable vehicle, as active components (i)–(iii) wherein
   (i) is an iodinated vegetable oil containing about 37 to 42 percent combined iodine,
   (ii) is a mucopolysaccharidase selected from the group consisting of thiomucase and hyaluronidase, and
   (iii) is escine.

2. The composition of claim 1 wherein said iodinated vegetable oil is the ethyl ester of iodinated poppy seed oil containing 37 to 40 percent by weight combined iodine.

3. The composition of claim 1 wherein said escine is in the form of its free acid.

4. The composition of claim 1 wherein said escine is in the form of a horse chestnut extract containing 70 percent by weight escine.

5. The composition of claim 1 wherein said iodinated vegetable oil is the ethyl ester of poppy seed oil, said mucopolysaccharidase is hyaluronidase and said escine is α-escine.

6. The composition of claim 1 wherein said iodinated vegetable oil is present in an amount sufficient to provide 1 to 15 weight percent of combined iodine relative to the total weight of said composition.

7. The composition of claim 1 wherein said iodinated vegetable oil is present in an amount sufficient to provide 1.5–6 weight percent of combined iodine relative to the total weight of the composition.

8. The composition of claim 1 wherein said mucopolysaccharidase is present in an amount sufficient to provide from 500 to 50,000 TRU in said composition.

9. The composition of claim 1 wherein the said escine is present in an amount ranging between 0.2 to 2% by weight of the total weight of said composition.

10. A process for treating cellulitis or folds of fat, comprising applying to those parts of the body to be treated, an effective amount of the composition of claim 1; massaging said composition into the parts of the body to which it has been applied and continuing this treatment daily for a period of time ranging between 1 and 4 months.

11. A composition for treating cellulitis or folds of fat comprising in a cosmetically acceptable vehicle, as active components (i)–(iii) wherein
  (i) is the ethyl ester of iodinated poppy seed oil containing about 37–40 percent combined iodine present in an amount sufficient to provide 1 to 15 percent by weight of combined iodine relative to the total weight of said composition,
  (ii) is a mucopolysaccharidase selected from thiomucase and hyaluronidase present in an amount sufficient to provide from 500 to 50,000 TRU in said composition; and
  (iii) is escine in the form of its free acid or in the form of a horse chestnut extract containing 70 percent escine present in an amount ranging between 0.2 and 2 percent by weight of the total weight of said composition.

* * * * *